United States Patent [19]

Diesen

[11] Patent Number: 4,814,527
[45] Date of Patent: Mar. 21, 1989

[54] CATALYTIC PROCESS FOR ETHYLENE DICHLORIDE

[75] Inventor: Ronald W. Diesen, Midland, Mich.

[73] Assignee: The Dow Chemical Company, Midland, Mich.

[21] Appl. No.: 68,218

[22] Filed: Jun. 25, 1987

Related U.S. Application Data

[63] Continuation of Ser. No. 866,559, May 23, 1986, abandoned, which is a continuation of Ser. No. 611,447, May 17, 1984, abandoned, which is a continuation-in-part of Ser. No. 434,995, Oct. 18, 1982, abandoned.

[51] Int. Cl.$^4$ .............................................. C07C 17/15
[52] U.S. Cl. .................................. 570/243; 570/245; 585/642
[58] Field of Search ................. 570/243, 245; 585/642

[56] References Cited

U.S. PATENT DOCUMENTS

| | | |
|---|---|---|
| 2,442,285 | 5/1948 | Cheney . |
| 3,363,010 | 1/1968 | Schwarzenbek . |
| 3,454,661 | 7/1969 | Hornig et al. . |
| 3,546,306 | 12/1970 | McCarthy . |
| 3,720,723 | 3/1973 | Pritchett . |
| 3,926,847 | 12/1975 | Beard et al. . |
| 4,167,528 | 4/1979 | Uriarte et al. . |
| 4,170,571 | 10/1979 | Ritscher . |
| 4,226,812 | 10/1980 | Pieters et al. . |
| 4,384,159 | 5/1983 | Diesen . |

FOREIGN PATENT DOCUMENTS 2095244  9/1982  United Kingdom .

*Primary Examiner*—Howard T. Mars
*Attorney, Agent, or Firm*—Marie F. Zuckerman; Paul D. Hayhurst

[57] ABSTRACT

Monosubstituted saturated lower hydrocarbons are oxyhalogenated selectively to saturated dihalohydrocarbons at 180°–350° C. in the presence of a catalyst which is formed by depositing a variable valence metal compound on a zeolitic support in such a manner that the catalyst can be employed to selectively produce ethylene dichloride and ethylene from ethyl chloride.

17 Claims, No Drawings

CATALYTIC PROCESS FOR ETHYLENE DICHLORIDE

CROSS-REFERENCE TO RELATED APPLICATION

This application is a continuation of application Ser. No. 886,559, filed May 23, 1986, which is a continuation of application Ser. No. 611,447, filed May 17, 1984, now abandoned, which latter is a continuation-in-part of application Ser. No. 434,995, filed Oct. 18, 1982, now abandoned.

BACKGROUND OF THE INVENTION

This invention relates to a catalytic halogenation process. More specifically, it relates to specific catalysts for use in the oxyhalogenation and disproportionation of halogenated hydrocarbons.

Ethylene dichloride (1,2-dichloroethane) is useful in that it may be dehydrohalogenated to vinyl chloride (chloroethene). Ethylene dichloride has been prepared in the past by the chlorination of ethylene using molecular chlorine and by the catalytic oxychlorination of ethylene. Several oxychlorination catalysts are known. For example, U.S. Pat. No. 3,892,816 describes the catalytic oxychlorination of ethylene by contacting ethylene, hydrogen chloride and molecular oxygen at a temperature of from about 450° F. to about 670° F. in the presence of a supported, stabilized cupric chloride catalyst. U.S. Pat. No. 3,634,330 discloses an oxychlorination catalyst composed of mixtures of cupric chloride and at least one alkali metal chloride or alkaline earth metal chloride supported on spheroidal particles formed mainly of hydrated silica but including certain metal oxides.

It is generally known that saturated compounds may be oxyhalogenated. A primary drawback of known processes for the oxyhalogenation of saturated compounds is their inability to selectively produce compounds which are less than fully halogenated. Thus, an attempt to produce dichloroethane from saturated compounds via known oxychlorination processes typically results in a product mixture which contains a full spectrum of chlorinated compounds which typically are fairly difficult to separate. Another drawback of said oxychlorination processes is their high operating temperatures. Additionally, a high temperature process is typically more expensive to operate than a process operated at a lower temperature. High temperatures are conducive to the cracking of ethylene dichloride to produce vinyl chloride and other more highly chlorinated compounds in the product. For example, U.S. Pat. No. 4,226,812 discloses a process wherein ethylene is oxychlorinated to ethylene dichloride, with coproduction of major amounts of vinyl chloride via thermal cracking, at temperatures ranging from 350° to 525° C. using a catalyst consisting essentially of a mixture of copper chloride and an alkali metal chloride irreversibly melt-occluded in a molecular sieve. The process also produces chlorotrifluoroethylene from 1,1,2-trichloro-1,2,2-trifluoroethane in low conversion.

It would be advantageous to have a process for the production of ethylene dichloride which could use ethane as a starting material, as ethane has a lower energy input than ethylene. It also would be advantageous to have a process for the production of ethylene dichloride from saturated compounds which could be operated at a lower temperature than conventional processes for the oxychlorination of saturated compounds, and, perhaps more importantly, which could produce ethylene dichloride with very high selectivity. Additionally, it would be advantageous to have a process which could coproduce ethylene dichloride and ethylene. The ability to produce ethylene as a coproduct would be a further utility since the coproduced ethylene could be chlorinated using molecular chlorine to achieve an overall balanced process for vinyl chloride production.

Known oxychlorination catalysts are not capable of selectively producing ethylene dichloride from ethyl chloride (chloroethane). Nor are said catalysts capable of selectively converting ethyl chloride to ethylene and ethylene dichloride. The catalysts employed in the patents cited hereinabove all are copper-containing catalysts for the conversion of ethylene to ethylene dichloride or vinyl chloride.

U.S. Pat. No. 3,926,847 discloses a catalyst containing a polyvalent metal halide on a support which contains a synthetic aluminosilicate of mixed layer crystal structure with randomly alternating layers of montmorillonite-like and mica-like structure. The support optionally contains a synthetic crystalline zeolitic component. Said catalyst produces a "larger mole ratio of the highly chlorinated reaction products containing no hydrogen to the partially chlorinated reaction products." Thus, the catalyst is not disclosed to be capable of selectively producing ethylene dichloride and ethylene from ethyl chloride.

U.S. Pat. No. 3,987,118 discloses a process for the oxychlorination of ethane by reacting, e.g., ethane, oxygen and hydrogen chloride while in the presence of a synthetic faujasite Y zeolite ion-exchanged with copper. The process produces a mixture of chlorinated compounds including 1,2-dichloroethylene, 1,1-dichloroethane, ethylene dichloride, trichloroethylene, vinyl chloride, and perchloroethylene.

U.S. Pat. No. 3,989,806 discloses a process for the oxidative destruction of chlorinated compounds in order to recover the chlorine value therefrom by reacting a chlorocarbon feed stream with oxygen at a temperature below 500° C. in the presence of at least one transition metal-containing supported catalyst. The preferred catalyst is a copper-exchanged zeolite.

U.S. Pat. No. 4,170,571 discloses a catalyst prepared by thoroughly ion-exchanging copper ions into zeolites of the ZSM-5 type. The catalyst is specifically designed to catalyze the complete combustion of hydrocarbons. Thus, it would be unsuitable for the selective production of ethylene dichloride and ethylene from ethyl chloride.

U.S. Pat. No. 4,167,528 discloses a cupric bromide catalyst on a zeolite support having a nominal pore size of about 10 angstroms. The catalyst is specifically suited to the production of tetrabromoethylene from butane.

Thus, many copper-containing catalysts are known, but none are known for the selective production of ethylene dichloride and ethylene from ethyl chloride.

Heretofore, a highly selective, energy saving, catalytic process for the preparation of ethylene dichloride (and ethylene) from ethyl chloride has not been disclosed. Such a process would be advantageous in that ethyl chloride may be prepared from ethane. Therefore, ethylene dichloride could be produced without using ethylene as a raw material as the production of ethylene by conventional processes is a very energy intensive process.

SUMMARY OF THE INVENTION

In one aspect, the present invention is such a process of selectively preparing ethylene dichloride and ethylene, or other saturated dihalohydrocarbons and corresponding alkenes by contacting oxygen, a mono-substituted saturated lower hydrocarbon, and optionally a hydrogen halide in the presence of a catalyst of this invention under relatively mild conditions. Surprisingly, the practice of said process requires only one step to produce the desired products at relatively low temperatures with very high selectivities.

In another aspect, this invention is the discovery of novel catalyst systems consisting essentially of (1) at least one compound including copper and chlorine atoms;
(2) at least one zeolite; and optionally
(3) at least one binder; and optionally at least one modifier, which catalyst can be employed to selectively produce ethylene and ethylene dichloride from ethyl chloride. These catalyst systems promote the highly selective conversion of ethyl chloride to ethylene dichloride and ethylene at unexpectedly low temperatures, and resist coking.

DETAILED DESCRIPTION OF THE INVENTION

The process of the present invention requires oxygen, a monosubstituted saturated lower hydrocarbon, and a catalyst of the present invention. A hydrogen halide is optionally employed, depending on the relative ratio of the products desired, as is described hereinafter.

The monosubstituted saturated lower hydrocarbons suitable for use in the process of the present invention are saturated hydrocarbons having from 2 to 6 carbon atoms and further having one substituent which is not hydrogen. Suitable non-hydrogen substituents include OH, Cl, Br, F, and I. The preferred non-hydrogen substituents are OH and Cl, with Cl being most preferred. Suitable monosubstituted saturated lower hydrocarbons include ethyl chloride, ethyl alcohol, ethyl bromide, 1-chloropropane, 2-chloropropane and the like. Preferred monosubstituted saturated lower hydrocarbons are ethyl chloride and ethyl alcohol, with ethyl chloride being most preferred. Other suitable starting materials which may be oxyhalogenated with the catalyst of the present invention include unsaturated lower hydrocarbons such as ethylene, propane, butenes and the like.

The feed gases can be used in any ratios which give the desired products. Typically, molar ratios of oxygen to monosubstituted saturated lower hydrocarbons of from about 0.1 to about 5 are employed, any suitable source of oxygen may be employed, including air, commercially pure oxygen and the like. Nitrogen, which is preferred, or other inert gases may be employed to dilute the feed gas stream. The inert gas may be employed in any practical ratio, although care should be taken to avoid explosive mixtures.

A hydrogen halide can be employed in any reaction of the present invention, as dictated by the stoichiometry of the desired reaction. Typically, molar ratios of hydrogen halide to monsubstituted saturated lower hydrocarbons of from about zero to about 4 are employed. A hydrogen halide preferably is employed in an excess of from about one to about 100 percent of the amount of the hydrogen halide required by the stoichiometry of the reaction is employed. The hydrogen halide typically is chosen so that the halide is the same as the halogen substituents on the saturated dihalohydrocarbon product. Hydrogen chloride is the preferred hydrogen halide. In the case of halogenated starting materials, hydrogen halide will form in situ if no hydrogen halide is employed as a raw material, however, some ethylene may be sacrificed.

The novel catalysts of the present invention are compositions having a variable valence metal compound deposited on a zeolite in such a manner that the catalyst can be employed to selectively produce ethylene and ethylene dichloride from ethyl chloride under reaction conditions. Advantageously, at reaction conditions at which ethylene and ethylene dichloride are selectively produced, the catalyst exhibits controlled coking or no coking. For the purposes of the present invention, the term "controlled coking" means that the catalyst may be used under reaction conditions in a fixed bed reactor continuously for at least about 24 hours without regeneration. Suitable variable valence metals include, for example, copper and iron. Copper is the preferred variable valence metal. The original anion of the variable valence metal compound is immaterial, since said anion will be replaced with a halogen during the oxyhalogenation process to form the active catalyst. For example, in an oxychlorination process hydrogen chloride will contact the original variable valence metal compound and a chloride compound will be formed and will be the active catalyst. Chloride is the preferred anion for the variable valence metal compound for oxychlorination reactions. Thus, copper chloride is the preferred variable valence metal compound for use in oxychlorinations. Copper chloride is usually employed as cupric chloride, but it may be employed as cuprous chloride or mixtures of both.

Any synthetic or naturally-occurring zeolite can be employed as a zeolitic component of the catalyst of the present invention. Suitable zeolites include, for example, conventional A-, X-, and Y-type zeolites, offretite, mordenite, chabazite, erionite, and synthetic siliceous zeolites such as, for example, silicalite, ZSM-5, ZSM-8, ZSM-11 and the like. Additionally, synthetic zeolites having other metals substituted for aluminum atoms can be employed. Preferred zeolitic supports have an average pore diameter of from about 4 to about 11 angstroms. Zeolites of the faujasite type are examples of preferred zeolites. More preferred zeolites have an average pore diameter of from about 6 to about 10 angstroms. See U.S. Pat. No. 3,140,322 for a more detailed discussion of some typical zeolites.

The synthetic siliceous zeolites employed in the present invention are well-known in the art. ZSM-5 has been described in U.S. Pat. No. 3,702,886. Silicalite is further described as crystalline silica which after calcination in air at 600° C. for one hour produces a silica polymorph having a mean refractive index of 1.39±0.01 and a specific gravity at 25° C. of 1.70±0.05 g/cc. Silicalite has been described in U.S. Pat. No. 4,061,724. D. H. Olson et al., writing in *J. of Catalysis*, 61, 390–396 (1980) clarified the various zeolite structures related to ZSM-5 and concluded that highly siliceous pentasil structures such as silicalite have properties in conformity with and directly related to the level of aluminum content. Therefore, silicalite may be considered as an end member of a substitutional series, e.g., a substantially aluminum-free form of ZSM-5. For the above teachings, these references are herein incorporated by reference in their entireties. The zeolites typically are employed in either an alkali metal or hydrogen ion form.

The catalyst of the present invention is prepared by depositing at least one variable valence metal compound onto the zeolitic support in such a manner that the catalyst is capable of selectively producing ethylene and ethylene dichloride from ethyl chloride. Preferably, the catalyst is prepared in such a manner that the catalyst is capable of selectively producing ethylene and ethylene dichloride from ethyl chloride at 250° C. and about atmospheric pressure while exhibiting no coking or controlled coking. The catalyst typically is prepared by applying a solution of the variable valence metal compound to the zeolitic support by any method which wets the porous support to the point of incipient wetness. For example, the technique termed "dry impregnation" or "impregnation to incipient wetness", which is referred to in *Heterogeneous Catalysis in Practice*, by C. N. Satterfield (1980) at pp. 82–83, can be used to prepare the catalyst. Typically, the solution is sprayed or sprinkled onto the zeolitic support. No additional special processing or preparation of the catalyst is required other than conventional procedures such as drying to remove the solvent of the solution, and calcining in order to remove organic residues. The calcination temperature typically is such that the variable valence metal compound is not volatilized substantially. Preferably, the calcination temperature is about 300° C. or less.

Advantageously, the catalyst contains a catalytic amount of at least one variable valence metal compound. Typically, the amount of variable valence metal compound used is such that the catalyst contains between about 0.5 and about 20 weight percent of the variable valence metal, calculated as the uncombined metal, based on the dried weight of the zeolite.

The catalyst of the present invention preferably includes at least one modifier of the type employed with known oxychlorination catalysts. Examples of these well known modifiers include alkali metals and their salts, and alkaline earth metals and their salts. Preferred modifiers include the chloride salts of the alkali metals. Typically, from about zero to about 10 weight percent of the modifier metal is employed based on the dried weight of the zeolite. Preferably, from about 0.5 to about 5 weight percent of modifier is employed. The modifier typically is added to the zeolite concurrently with the variable valence metal compound and in the same manner.

In addition, the catalyst can contain an optional binder. The binder can be a mixture of binders. It serves to provide mechanical strength to the catalyst in pelletized form and provides additional surface area on which to deposit the variable valence metal compoound. The binder preferably is substantially inert under the reaction conditions employed in the production of ethylene dichloride (and ethylene) from ethyl chloride. The preferred binder is silica gel. If employed, the binder typically is employed in an amount sufficient to enhance the mechanical strength of catalyst pellets. Typically, the amount of binder employed ranges from about 5 to about 80 weight percent of the total weight of the final catalyst.

The catalyst of the present invention has a surface area characteristic of a zeolite. In other words the catalyst composition has a very high surface area which is similar to the surface area of the zeolite component of the catalyst. The surface area of the catalyst may be reduced somewhat in the case of catalysts which include a binder. Preferably, however, the catalyst of the present invention will have a surface area of at least about 150 $m^2/g$; most preferably, the surface area will be at least about 200 $m^2/g$.

The catalyst is placed in a reaction zone in such fashion as to allow the rapid passage of vapor or gas therethrough. For example, the catalyst can be employed in any conventional reactor bed, such as, for example, a fixed bed or a fluidized bed.

The process of the present invention is advantageously conducted at any temperature at which a saturated dihalohydrocarbon and a corresponding alkene are produced selectively. Preferably when chlorinated products are desired, the process is conducted at a temperature of from about 180° C. to about 350° C.; most preferably it is conducted at from about 200° C. to about 300° C. As mentioned hereinbefore, one of the major advantages of the process of the present invention is that it can selectively convert ethyl chloride to ethylene dichloride and ethylene at unexpectedly low temperatures, i.e., at temperatures below about 300° C. Ordinarily, the reaction will proceed at atmospheric pressure or higher, but subatmospheric pressures may be employed if desired.

The catalyst of the present invention can operate with controlled coking under the reaction conditions employed in the production of ethylene dichloride and ethylene from ethyl chloride. It is typical for the catalyst of the present invention to operate under these conditions for up to about 100 hours or more. If regeneration, or decoking, is required the reactor periodically can be shut down and the carbon or coke formation, if any, can be removed, usually by burning off, that is, by heating the reactor in the presence of oxygen or air. Usually a comparatively mild temperature in the range of about 225° C. to about 300° C. is sufficient to remove the coke formation from the catalysts of the present invention.

Without being bound by the following theory, and without being limited to it, it is presented to promote a more complete understanding of the invention. The catalyst of the present invention has two essential components, these being a zeolite component and a variable valence metal compound component. For this theoretical discussion, copper chloride is the variable valence metal compound, and ethyl chloride is the monosubstituted saturated lower hydrocarbon. The catalyst is prepared in such a way that relatively little, if any, ion exchange occurs, thereby resulting in the deposition of copper chloride on the outer surface of the zeolite. Considering an isolated zeolite crystallite, ethyl chloride introduced to the catalyst under reaction conditions can enter the internal structure of the zeolite where it will be converted to ethylene and HCl, e.g., as taught in U.S. Pat. No. 4,384,159. The ethylene freely evolves out of the zeolite where it contacts the active copper chloride species on the outer surface of the zeolite crystallite and is partially converted to ethylene dichloride. The active copper chloride species is regenerated by oxychlorination with HCl. Ethylene dichloride is too large to freely reenter the zeolite, wherein it could be dehydrohalogenated to vinyl chloride. This substantially prevents the formation of tri- and higher-chlorinated by-products through subsequent reaction. Therefore, ethylene dichloride is selectively produced.

The process selectively produces ethylene and ethylene dichloride. The relative amount of each in the reactor effluent is easily varied over a wide continuum, from mostly ethylene to essentially all ethylene dichloride. Generally speaking, the presence of HCl in the reaction feed tends to favor the production of ethylene dichloride. However, at relatively high temperatures the dehydrohalogenation rate increases relative to the rate of oxychlorination, thus favoring the production of ethylene. The following reactions are examples of the effect of the feed composition on the effluent composition:

Disproportionation:

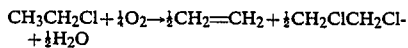

Oxychlorination:

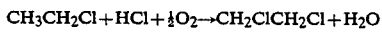

For a given feed composition, the process temperature and the copper chloride content of the catalyst can be selected to balance the rates of dehydrohalogenation and oxychlorination to give the desired ratio of ethylene to ethylene dichloride.

The theory additionally proposes that the copper chloride on the outside of the zeolite serves to control coking by catalytic oxidation of coke as it forms.

The reaction or contact time of the monosubstituted saturated lower hydrocarbon with the catalyst in the reactor can be varied. The contact time necessary between the monosubstituted saturated lower hydrocarbon and catalyst to promote the desired oxyhalogenation reaction is obtained by controlling the space velocity of the gaseous material passing through the reaction zone. The contact time is dependent upon several factors, namely, the scale of the operation, the quantity of catalyst in the reactor, and the type of reactor employed. For most reactors a contact time as high as about 25 seconds or more and as low as 0.5 second can be employed. If the contact time is too low the quantity of unreacted monosubstituted saturated lower hydrocarbon coming over is too high. On the other hand, if the contact time is too high, that is, much above 25 seconds, the impurities increase which makes it more difficult to recover the desired compound in a pure form. One can readily adjust the gaseous feed rate to obtain the optimum reaction or contact time for any particular type reactor. Feed rates of the various components may be individually adjusted so as to provide maximum selectivity to the desired product with respect to the particular apparatus employed, catalyst concentration, pressure and temperature.

When the monosubstituted saturated lower hydrocarbon contacts the catalyst under the conditions described hereinbefore, the monosubstituted saturated lower hydrocarbon is converted selectively into a saturated dihalohydrocarbon and alkene. The gaseous mixture that is withdrawn from the reaction zone can be passed directly to a condenser thereby recovering the condensable materials while allowing the non-condensables, such as ethylene, to pass overhead and be recycled. The condensables may be separated into the desired dihalogenated product and recyclable materials such as, for example, unreacted ethyl chloride in the case where ethyl chloride is the monosubstituted saturated lower hydrocarbon. Ethylene dichloride and ethylene are the most preferred products of the process of the present invention.

For the purposes of the present invention, the following definitions are employed. The term "selectively", as used in the phrase "selectively converted", means that a selectivity of at least about 60 mole percent or volume percent is achieved.

Selectivity is generally defined as the expression of the amount of a desired product as a fraction or percentage of the theoretically possible amount from the feed material converted. In the process of the present invention it is desirable to simultaneously coproduce a saturated dihalohydrocarbon and the corresponding alkene. Thus, for the purpose of the present invention, "selectivity" is specifically defined as selectivity to a saturated dihalohydrocarbon and the corresponding alkene based on monosubstituted saturated lower hydrocarbon reacted, and is calculated using the following equation:

$$\% \text{ selectivity} = (100)(Y)/(Y+Z)$$

wherein Y is moles of saturated dihalohydrocarbon plus moles of corresponding alkene in the product stream, and wherein Z is moles of organic by-products in the reactor effluent stream. A sample calculation for selectivity follows Table I.

Typically, a selectivity of at least about 70 mole percent is achieved in the production of a saturated dihalohydrocarbon and the corresponding alkene from a monosubstituted saturated lower hydrocarbon; preferably the selectivity is at least about 80 mole percent; more preferably the selectivity is at least about 90 mole percent; most preferably, it is at least about 95 mole percent.

SPECIFIC EMBODIMENTS

The following examples are given to illustrate the invention, but are not to be construed as limiting its scope. All parts and percentages are by weight unless otherwise indicated.

EXAMPLE 1

A copper chloride impregnated catalyst is prepared using the incipient wetness technique. Pellets of Linde molecular sieve S115 silicalite (lot 8251-1-2) containing 15 percent silica as a binder is crushed and sieved to a size of 7-12 mesh. A solution is prepared by dissolving 60 g of $CuCl_2 2H_2O$ in 100 cc of water. A 6-g sample is placed in a glass cylindrical vessel and is wetted slowly with the solution until no more solution is drawn into the porous particles. The particles are then removed from the vessel and are contacted briefly with a paper towel in order to remove excess liquid from the surface of the particles. The wetting process uses 5 cc of the solution. The wetted catalyst, having a mass of 10.7 g, is dried at a temperature of 125° C. for approximately 2 hours. The dried catalyst has a mass of 7 g, and is gray-tan in color.

A 6.3-g sample of the dried catalyst is placed in a glass reaction vessel. The vessel has a nominal outside diameter of ½ inch and is equipped with a means for uniform heating of the outer wall and with a temperature measuring means which is in a well in the center of the bed of catalyst. The bed of catalyst in the reaction vessel has a height of 4.25 inches. The reaction vessel is heated to a temperature of 220° C. overnight in order to calcine the catalyst.

EXAMPLES 2-4

A number of reactions are performed and the results are summarized in Table I. For each reaction, a 21-stage static mixer is used to thoroughly mix the reactants, all of which are in the gas phase, to form a gaseous mixture. Individual gas flow rates are measured and controlled by calibrated flow meters. A gas chromatograph having thermal conductivity and flame ionization detectors is employed to determine the composition of the gaseous mixture before and after it passes through the catalyst bed.

TABLE I

|  | Ex. 2 | Ex. 3 | Ex. 4 |
|---|---|---|---|
| $O_2$ cc/min | 10 | 15 | 10 |
| air cc/min | 15 | — | 15 |
| $N_2$ cc/min | — | 25 | — |
| HCl cc/min | 7 | 9 | 10 |
| ethanol cc/min | — | — | 9.3 |
| ethyl chloride cc/min | 11 | 12 | — |
| Temperature °C. | 255 | 275 | 255 |
| Conversion of ethyl chloride (volume %) | 45% | 60% | — |
| Conversion of ethanol (volume %) | — | — | 90+% |
| Reactor Effluent Stream Organic Analysis (volume %) |  |  |  |
| ethyl chloride | 55 | 40 | 59 |
| ethylene | 6 | 16 | 13 |
| ethylene dichloride | 38 | 43 | 27 |
| dichloroethylene | * | * | * |
| 1,1,2-trichloroethane | * | * | * |
| 1,1,2,2-tetrachloroethane | * | * | * |
| Ratio of ethylene dichloride to ethylene | 6.3 | 2.7 | 2.1 |
| % Selectivity to ethylene and ethylene dichloride | 97.8 | 98.3 | 97.6 |

*Trace amount, sum of trace amounts is less than 1 volume percent for each Example. $CO_2$ is also observed in an amount which is less than 1 volume percent of the effluent.

It may be observed from Table I that the catalyst and process of the present invention provide conversion of monosubstituted saturated lower hydrocarbons to ethylene dichloride and ethylene with exceptionally high selectivity, as the total amount of by-products produced is less than one volume percent of the product stream in each case. The percent selectivity is calculated using the formula % selectivity = $100(Y)/(Y+Z)$ as defined hereinabove. For Example 2: $Y = 6+38 = 44$; $Z = <\pm 1$. Therefore, % selectivity = $4400/(44+1) = 97.777 = 97.8\%$ selectivity to ethylene and ethylene dichloride.

EXAMPLE 5

A copper chloride-potassium chloride catalyst is prepared using the incipient wetness technique. Pellets of synthetic faujasite (Linde Molecular Sieve 30-200, Lot 968030201) in the sodium form, a Y-type zeolite, is dried at 125° C. Large pore silica gel (No. 89384 obtained from Alfa Division of Morton Thiokol, Inc.) is dried at 125° C. The faujasite (7.5 g) is mixed with 2.5 g of the silica gel. The mixture is compacted at 50,000 pounds per square inch to make pellets having a diameter of ⅛th inch. The pellets are placed in an oven having a temperature of 125° C. for a period of three days. The heated pellets are then calcined at 400° C. for 2 hours, yielding 9.06 g of calcined pellets. Then, 60 g of $CuCl_2.2H_2O$ and 6 g of KCl are added to 100 cc of water to form a solution. A 3.8 g sample of calcined pellets is placed in a glass cylindrical vessel and is wetted slowly with the solution until no more solution is drawn into the porous particles. The particles are then removed from the vessel and are contacted briefly with a paper towel in order to remove excess liquid from the surface of the particles. The wetting process uses 4 cc of the solution. The wetted catalyst, having a weight of 7.4 g and a light-green color, is dried at a temperature of 125° C. for several hours. The dried catalyst has a mass of 5 g and is tan-brown in color.

A 5 g sample of the the dried catalyst is placed in the reaction vessel of Example 1 and is calcined using the method of Example 1 except that the temperature of 200° C.

EXAMPLES 6-7

A number of reactions are performed using the general procedure of Examples 2-4, except that the catalyst of Example 5 is employed. The results are summarized in Table II.

TABLE II

|  | Ex. 6 | Ex. 7 |
|---|---|---|
| $O_2$ cc/min | 3 | 3 |
| air cc/min | — | — |
| $N_2$ cc/min | — | — |
| HCl cc/min | 10 | 10 |
| ethanol cc/min | — | — |
| ethyl chloride cc/min | 15 | 15 |
| Temperature °C. | 225 | 260 |
| Conversion of ethyl chloride (volume %) | 35 | 60 |
| Conversion of ethanol (volume %) | — | — |
| Reactor Effluent Stream Organic Analysis (volume %) |  |  |
| ethyl chloride | 65 | 40 |
| ethylene | 9 | 35 |
| ethylene dichloride | 25 | 24 |
| dichloroethylene | * | * |
| 1,1,2-trichloroethane | * | * |
| 1,1,2,2-tetrachloroethane | * | * |
| Ratio of ethylene dichloride to ethylene | 2.8 | 0.69 |
| Selectivity to ethylene and ethylene dichloride | 97.1 | 98.3 |

*Trace amount, sum of trace amounts is not greater than 1 volume percent for each Example. $CO_2$ and CO also are observed in an amount which is <1 volume percent of the effluent.

Examples 6 and 7 demonstrate the effect of temperature on the ratio of ethylene dichloride to ethylene in the effluent stream for a given feed composition. Examples 6 and 7 also demonstrate unprecedented selectivity to ethylene and ethylene dichloride.

COMPARATIVE EXPERIMENT 1

A 12 g sample of ZSM-5 is ion-exchanged for two hours with 250 cc of a solution having 670 g of $Cu(NO_3)_2.3H_2O$ in 1000 ml of distilled water. The exchange procedure is repeated twice using fresh solution and the zeolite is filtered after each exchange. The final filtered material is washed with 200 ml of distilled water. The resulting copper-exchanged zeolite is dried overnight at 125° C. and is light blue (robin egg blue) in color.

The catalyst is similar, if not identical, to the catalyst of U.S. Pat. No. 4,170,571, cited hereinabove.

COMPARATIVE EXPERIMENT 2

A 4.68 g sample of the dried exchanged zeolite of Comparative Experiment 1 is added to the empty glass reaction vessel of Example 1 and is held at 400° C. overnight. The reaction vessel is then maintained at 250° C. while a feed stream is introduced to the reaction vessel. The feed stream is 4 cc/min ethylene dichloride, 10 cc/min HCl, 10 cc/min $O_2$ and 8 cc/min air. During the ensuing one-hour period the only major reaction products are observed to be CO and CO$_2$, and the conversion of ethylene dichloride is approximately 10 volume percent. Rapid deactivation of the exchanged catalyst is observed, i.e., the activity of the catalyst decreases by 10-20 percent in the one-hour period, and prevents determination of steady state reaction values.

Comparative Experiment 2 demonstrates the rapid deactivation of a copper-exchanged zeolite catalyst in the presence of ethylene dichloride, oxygen and HCl.

As mentioned before, the above examples and comparative experiments serve only to illustrate the invention and its advantages, and they should not be interpreted as limiting since further modifications of the disclosed invention will be apparent to those skilled in the art. All such modifications are deemed to be within the scope of the invention as defined by the following claims.

What is claimed is:

1. A process for selectively converting a monosubstituted saturated lower hydrocarbon to a saturated dihalohydrocarbon and the corresponding alkene, comprising contacting in the vapor phase reactants consisting essentially of oxygen, a monosubstituted saturated lower hydrocarbon having a non-hydrogen substituent selected from the group consisting of Cl, Br, F, and I; and a hydrogen halide, in the presence of a catalyst at a temperature in the range from about 200° C. to about 300° C. and under reaction conditions such that a saturated dihalohydrocarbon and the corresponding alkene are selectively produced; said catalyst consisting essentially of (1) at least one compound including copper atoms and chlorine atoms in the form of chloride, and (2) at least one zeolite.

2. The process of claim 1 wherein the saturated dihalohydrocarbon and the alkene are produced in a selectivity of at least about 70 mole percent.

3. The process of claim 1 wherein the saturated dihalohydrocarbon and the alkene are produced in a selectivity of at least about 80 mole percent.

4. The process of claim 1 wherein the saturated dihalohydrocarbon and the alkene are produced in a selectivity of at least about 90 mole percent.

5. The process of claim 1 wherein the saturated dihalohydrocarbon and the alkene are produced in a selectivity of at least about 95 mole percent.

6. A process of claim 1 wherein the monosubstituted saturated lower hydrocarbon has from 2 to about 5 carbon atoms.

7. A process of claim 1 wherein the non-hydrogen substituent is Cl.

8. A process of claim 7 wherein the monosubstituted saturated lower hydrocarbon is ethyl chloride, the saturated dihalohydrocarbon is 1,2-dichloroethane, the alkene is ethylene, and the hydrogen halide is hydrogen chloride.

9. A process of claim 1 wherein the zeolite has an average pore diameter of from about 4 to about 11 angstroms.

10. A process for selectively converting a monosubstituted saturated lower hydrocarbon to a saturated dihalohydrocarbon and the corresponding alkene, comprising contacting in the vapor phase reactants consisting essentially of oxygen, a monosubstituted saturated lower hydrocarbon having a non-hydrogen substituent selected from the group consisting of Cl, Br, F, and I; and a hydrogen halide, in the presence of a catalyst at a temperature in the range from about 200° C. to about 300° C. and under reaction conditions such that a saturated dihalohydrocarbon and the corresponding alkene are selectively produced; said catalyst consisting essentially of (1) at least one compound including copper atoms and chlorine atoms in the form of chloride, and (2) at least one zeolite, and (3) at least one modifier selected from the group consisting of IA and IIA metals and metal salts.

11. The process of claim 10 wherein the modifier is a chloride of an alkali metal.

12. A process for selectively converting a monosubstituted saturated lower hydrocarbon to a saturated dihalohydrocarbon and the corresponding alkene comprising contacting in the vapor phase reactants consisting essentially of oxygen, a monosubstituted saturated lower hydrocarbon having a non-hydrogen substituent selected from the group consisting of Cl, Br, F, and I; and a hydrogen halide, in the presence of a catalyst at a temperature in the range from about 200° C. to about 300° C. and under reaction conditions such that a saturated dihalohydrocarbon and the corresponding alkene are selectively produced; said catalyst consisting essentially of (1) at least one compound including copper atoms and chlorine atoms in the form of chloride, (2) at least one zeolite, (3) at least one modifier selected from the group consisting of IA and IIA metals and metal salts, and (4) at least one binder.

13. A process for selectively converting ethyl chloride to ethylene dichloride and ethylene, comprising contacting in the vapor phase reactants consisting essentially of ethyl chloride, oxygen, and a hydrogen halide, in the presence of a catalytic amount of a catalyst consisting essentially of copper chloride, a zeolite, potassium chloride, and a silica binder; said contacting occurring at a temperature in the range from about 200° C. to about 300° C. and under other reaction conditions such that ethylene dichloride and ethylene and are selectively produced.

14. The process of claim 13 wherein the zeolite is silicalite, ZSM-5, or a zeolite of the faujasite type.

15. The process of claim 13 wherein the selectivity to ethylene dichloride and ethylene is at least about 80 mole percent.

16. The process of claim 13 wherein the selectivity to ethylene dichloride and ethylene is at least about 90 mole percent.

17. The process of claim 13 wherein the selectivity to ethylene dichloride and ethylene is at least about 95 mole percent.

* * * * *